United States Patent [19]

Schulte-Elte et al.

[11] Patent Number: 4,610,813
[45] Date of Patent: Sep. 9, 1986

[54] HYDROXYLIC CAMPHOLENIC ALDEHYDE DERIVATIVES, THEIR UTILIZATION AS PERFUME INGREDIENTS AND PERFUMING COMPOSITIONS CONTAINING SAME

[75] Inventors: Karl-Heinrich Schulte-Elte, Onex; Bernard L. Muller; Hervé Pamingle, both of Geneva, all of Switzerland

[73] Assignee: Firmenich SA, Geneva, Switzerland

[21] Appl. No.: 710,886

[22] Filed: Mar. 12, 1985

[30] Foreign Application Priority Data

Mar. 23, 1984 [CH] Switzerland .................. 1473/84

[51] Int. Cl.⁴ .................. A61K 7/46; C07C 35/06
[52] U.S. Cl. .................................. 252/522 R
[58] Field of Search .................. 568/838, 820; 252/522 R

[56] References Cited

U.S. PATENT DOCUMENTS

| | | | |
|---|---|---|---|
| 4,052,341 | 10/1977 | Naipawer et al. | 568/838 |
| 4,149,020 | 4/1979 | Kamath et al. | 568/838 |
| 4,173,585 | 11/1979 | Yoshida et al. | 568/838 |
| 4,210,767 | 7/1980 | Yoshida et al. | 568/838 |
| 4,219,451 | 8/1980 | Yoshida et al. | 568/838 |
| 4,318,831 | 3/1982 | Klein et al. | 568/838 |

OTHER PUBLICATIONS

Easter et al. "Chem. Abstr." vol. 93(15) p 149961s.
Easter et al, "Chem. Abstr." vol. 97(23) p 198415h.
Easter et al., "Chem. Abstr." vol. 97(23) p 198416j.
Kingston, "Chem. Abstr." vol. 102(17) p 146754v.

Primary Examiner—Werren B. Lone
Attorney, Agent, or Firm—Pennie & Edmonds

[57] ABSTRACT

Novel compounds of formula

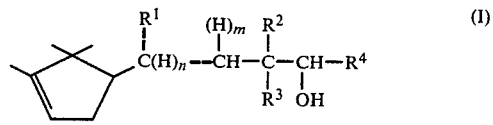

wherein:
a. $R^1=CH_3$; $n=m=1$; $R^2=CH_3$; $R^3=R^4=H$,
b. $R^1=CH_2$; $n=0$; $m=1$; $R^2=CH_3$; $R^3=R^4=H$,
C. $R^1=CH-CH_3$; $n=0$; $m=1$; $R^2=CH_3$; $R^3=R^4=H$,
d. $R^1=H$; $n=m=0$; $R^2=R^4=CH_3$; $R^3=C_2H_5$,
e. $R^1=H$; $n=m=0$; $R^2=R^3=R^4=CH_3$,
f. $R^1=H$; $n=m=0$; $R^2=CH_3$; $R^3=C_2H_5$; $R^4=H$,
g. $R^1=H$; $n=m=0$; $R^2=R^3=CH_3$; $R^4=H$,
h. $R^1=H$; $n=m=1$; $R^2=CH_3$; $R^3=C_2H_5$; $R^4=H$
i. $R^1=H$; $n=m=1$; $R^2=R^3=CH_3$; $R^4=H$ and wherein one of the dotted lines stands for a single carbon-carbon bond and the other one for a double bond, or each of them designates a single bond, possess odorous properties of sandalwood type and consequently can find a utility for the preparation of perfumes and perfumed products.

12 Claims, No Drawings

HYDROXYLIC CAMPHOLENIC ALDEHYDE DERIVATIVES, THEIR UTILIZATION AS PERFUME INGREDIENTS AND PERFUMING COMPOSITIONS CONTAINING SAME

BRIEF SUMMARY OF THE INVENTION

This invention provides novel hydroxylic derivatives of campholenic aldehyde. The compounds of the invention possess formula

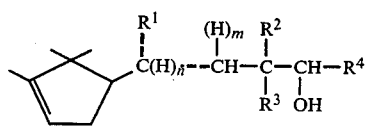

wherein:
a. $R^1=CH_3; n=m=1; R^2=CH_3; R^3=R^4=H$,
b. $R^1=CH_2; n=0; m=1; R^2=CH_3; R^3=R^4=H$,
c. $R^1=CH-CH_3; n=0; m=1; R^2=CH_3; R^3=R^4=H$,
d. $R^1=H; n=m=0; R^2=R^4=CH_3; R^3=C_2H_5$,
e. $R^1=H; n=m=0; R^2=R^3=R^4=CH_3$,
f. $R^1=H; n=m=0; R^2=CH_3; R^3=C_2H_5; R^4=H$,
g. $R^1=H; n=m=0; R^2=R^3=CH_3; R^4=H$,
h. $R^1=H; n=m=1; R^2=CH_3; R^3=C_2H_5; R^4=H$
i. $R^1=H; n=m=1; R^2=R^3=CH_3; R^4=H$ and wherein one of the dotted lines stands for a single carbon-carbon bond and the other one for a double bond, or each of them designates a single bond. Specific examples of the compounds defined by above given formula (I) are the following:

(−)-(E)-3,3-dimethyl-5-(2′,2′,3′-trimethyl-3′-cyclopenten-1′-yl)-4-penten-2-ol,
(−)-(1′S,E)-3-ethyl-3-methyl-5-(2′,2′,3′-trimethyl-3′-cyclopenten-1′-yl)-4-penten-2-ol,
(+)-(1′S)-2-methyl-4-(2′,2′,3′-trimethyl-3′-cyclopenten-1′-yl)-1-pentanol,
(−)-(1′R)-2-methyl-4-(2′,2′,3′-trimethyl-3′-cyclopenten-1′-yl)-4-hexen-1-ol,
(−)-(1′S)-2-methyl-4-(2′,2′,3′-trimethyl-3′-cyclopeten-1′-yl)-4-penten-1-ol,
(−)-(1′S,E)-2-ethyl-2-methyl-4-(2′,2′,3′-trimethyl-3′-cyclopenten-1′-yl)-3-buten-1-ol,
(−)-(1′S,E)-2,2-dimethyl-4-(2′,2′,3′-trimethyl-3′-cyclopenten-1′-yl)-3-buten-1-ol,
(−)-(1′,S)-2-ethyl-2-methyl-4-(2′,2′,3′-trimethyl-3′-cyclopenten-1′-yl)-1-butanol,
(+)-2,2-dimethyl-4-(2′,2′,3′-trimethyl-3′-cyclopenten-1′-yl)-1-butanol.

Compounds of formula (I) possess useful odorous properties and can be used advantageously for the preparation of perfumes and perfumed products. This invention provides also a perfume composition, a perfume base and a perfumed product containing as odor imparting or modifying ingredient an odor effective amount of one of the compounds of formula (I).

Further, the invention provides a perfumed product seleced from the group consisting of soap, liquid and solid powder detergent and fabric softener containing as odor imparting or modifying ingredient an odor effective amount of one of the compounds of formula (I).

BACKGROUND OF THE INVENTION

Certainly sandalwood oil is still nowdays one of the most precious elements to perfumers, not only for its intrinsic odorous characters, but also for the fixative properties it develops vis-a-vis a great variety of compositions of various nature. The prior art reports several synthetic products whose odorous properties can be assimilated to those shown by the natural oil. In this context, U.S. Pat. No. 4,052,341 describes a perfume composition consisting of a mixture of 3-methyl-5-(2,2,3-trimethylcyclopent-3-en-1-yl)-pentane-3-ol and of 6-(2,2,3-trimethylcyclopent-3-en-1-yl)-hexan-3-ol, two alcohols of formula

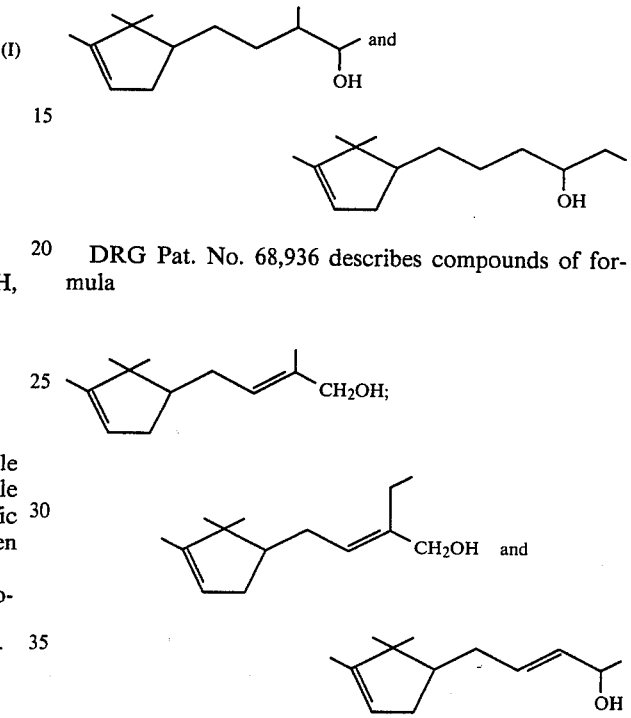

DRG Pat. No. 68,936 describes compounds of formula

The two former compounds possess an odor reminiscent of musk and sandalwood oil whereas the latter compound develops an odor reminiscent of fig with a slight cedarwood tonality.

A thorough investigation relative to the sandalwood type compounds has been published by E. J. Brunke and E. Klein [Essential Oils, Ed. B. D. Mookherjee and C. J. Mussinan, p. 83 and ff., Allured Publishing Corp. (1981)]. From this study, it becomes apparent that one of the efficient synthon for the preparation of this type of compounds is constituted by campholenic aldehyde of formula

This molecular moiety is in fact present in many of the prior art compounds.

Naipawer et al. [Essential Oils, op, cit, p. 105 and ff] investigated the possible relationship which could exist between molecular structure and sandalwood odor of some of the prior known compounds.

Their study was intended to identify the "structural" characters a given chemical must possess in order to develop the desired sandalwood oil odor.

It is interesting to note in this respect that none of the compounds examined by Naipawer et al. possesses a double substitution at the carbon in position 2 of the open chain. On the other hand, none of the described compounds possesses a substitution at the carbon atom in position 4 of the same open chain.

Several fragrance specialities have been created by using the cited prior known compounds and have appeared on the market in the course of the last few years under different tradenames. These are depicted hereinbelow.

| Speciality | Origin | Formula of the main constituent |
| --- | --- | --- |
| SANDALORE | L. Givaudan | (structure with OH) |
| SANDACORE | Kao Soap | (structure with OH) |
| BRAHMANOL | Dragoco | (structure with OH) |
| BACDANOL | Int. Flavors & Fragrances | (structure with OH) |

In view of the already existing compounds, one might have believed that perfumers possess, for their creation activity, a sufficiently broad spectrum of sandalwood fragrant raw materials.

In reality, it has become apparent that such is not the case. If it is true to say that each of the prior known compounds is able to confer a sandalwood note to the compositions into which it is incorporated, the specific effects achieved vary widely from one compound to the other. Their diffusiveness, for example, as wellas their substantivity can also vary as a function of the particular application to which they are destined. Though they all have been defined as sandalwood type compounds, none of them possess an identical odor character. The expert recognizes in fact that the typical sandalwood oil note is but the resultant of a number of different odorous notes reminiscent in turn of santalol, cedarwood oil or gaiac-wood oil, or of sweet, balsamic, slightly ambery, spicy, animal or transpiration-like notes or even of those milky notes reminiscent of freshly boiled milk.

It doesn't come as a surprise therefore to find that none of the known compounds suggested by the prior art can, when taken alone, replace natural sandalwood oil, each of them contributing to a greater or lesser extent to one or the other of its specific partial characters. This fact may sound astonishing when looking at the analogy, from the point of view of their structure, presented by the above cited known derivatives of campholenic aldehyde. This confirms once again the character of uncertainty which surrounds any speculation in the field of aroma chemicals where no known theory enables to correlate validly the molecular structure of a given chemical and its odor properties.

It should be mentioned moreover that in the case of "sandalwood" compounds, marked effects of anosima have been observed among both expert and lay people; several individuals in fact were not able to detect the odor developed by one or the other of the compounds submitted to their evaluation.

As a result of this situation, there is a permanent need to develop novel compounds of sandalwood fragrance character in order to enlarge the perfumer's palette and to enable him to broaden his creative skill.

THE INVENTION

The present invention offers a novel solution to this problem. We have discovered unexpectedly that the compounds of formula (I) possess odorous properties superior to those shown by the prior known derivatives of the art. This superiority appears not only with regard to their intrinsic odor type characters but, and especially, with regard to their fragrance strength and their substantivity. This fact may appear astonishing in view of the similarity which exists among the molecular structure of novel compounds (I) and those of the piror art. Even more astonishing is the fact that the identity and utility of said compounds (I) have remained unrecognized sofar and have escaped the attention of the many research groups which have devoted considerable effort to the study of sandalwood compounds, namely to those compounds having a campholenic aldehyde structural unity.

Each of the different compounds of formula (I), while characterized by a common note reminiscent of sandalwood, possesses its own specific and discreet fragrance, e.g. a balsamic, a milky and a cedar-like woody character. The expert of the art can, as a function of these different notes, chose the compound that better suits the specific application he has envisaged. For example, 2-methyl-4-(2,2,3-trimethyl-3-cyclopenten-1-yl)-4-penten-1-ol is the compound that better develops the typical scent of natural sandalwood oil. On the other hand, 3,3-dimethyl-5-(2,2,3-trimethyl-3-cyclopenten-1-yl)-4-penten-2-ol possesses a balsamic, sweet and milky secondary note, whereas 3-ethyl-3-methyl-5-(2,2,3-trimethyl-3-cyclopenten-1-yl)-4-penten-2-ol shows a more marked note reminiscent of cedarwood or undistilled sandalwood oil.

In spite of these differences, all the compounds of formula (I) are more powerful and olfactively more stable than the hitherto known analogous derivatives: in other terms, they are more performant than these latter. As a result of it, their utilisation is more advantageous in terms of the nature of the effect achieved and of the economy realized.

As it is often the case in perfumery, the proportions in which the compounds of the invention can be employed vary within a wide range. Concentrations of the order of 0.1% by weight can be used to perfume various articles such as soaps, shampoos, cosmetics, solid or liquid detergents, body deodorizers, room fresheners or household articles.

High concentrations are suitable to the preparation of perfumes and colognes. Of course, the said values cannot be interpreted restrictively since they primarily depend on the nature of the product it is desired to perfume, on that of the perfume coingredients present in a given composition and especially on the effect it is desired to achieve.

The compounds of the invention perfectly match with most of the ingredients of current use in perfumery. The identity of the said ingredients is common knowledge to the expert and their enumeration here appears therefore superfluous; reference is made however to European Patent application published under No. 0,096,243.

The compounds of the invention are prepared according to original and economical processes starting from campholenic aldehyde, a derivative of α-pinene, a by-product of turpentine oil.
The processes followed are illustrated by the reaction schemes given hereinbelow.
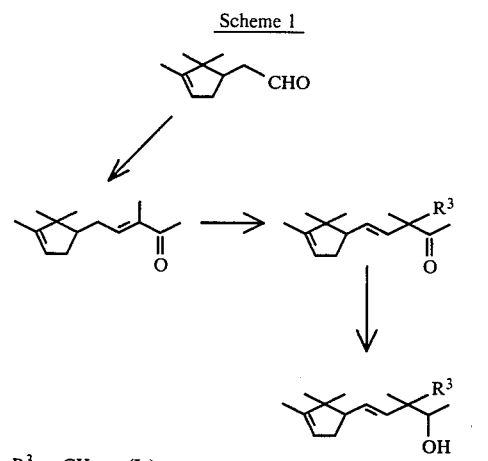
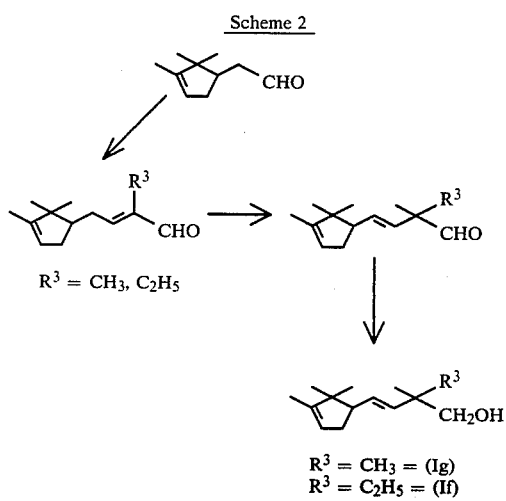
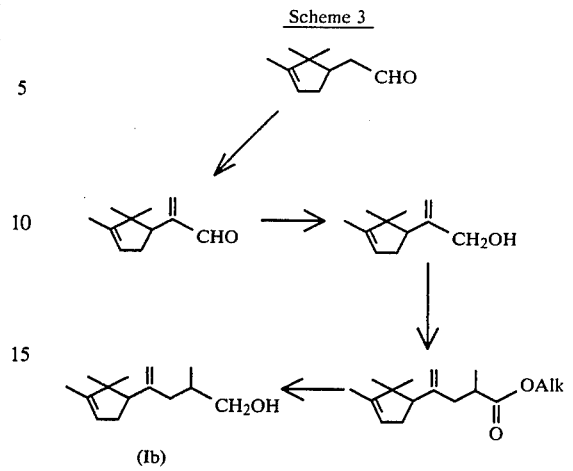
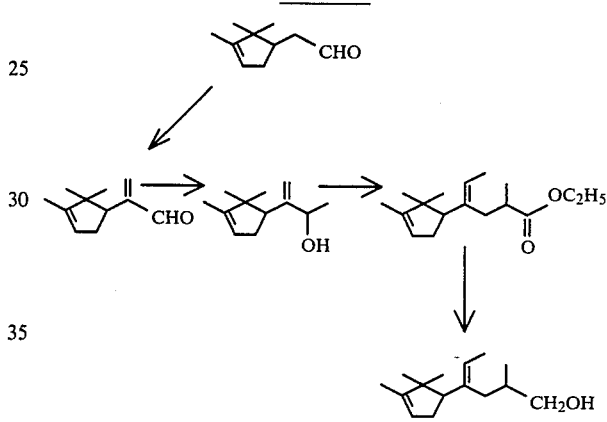
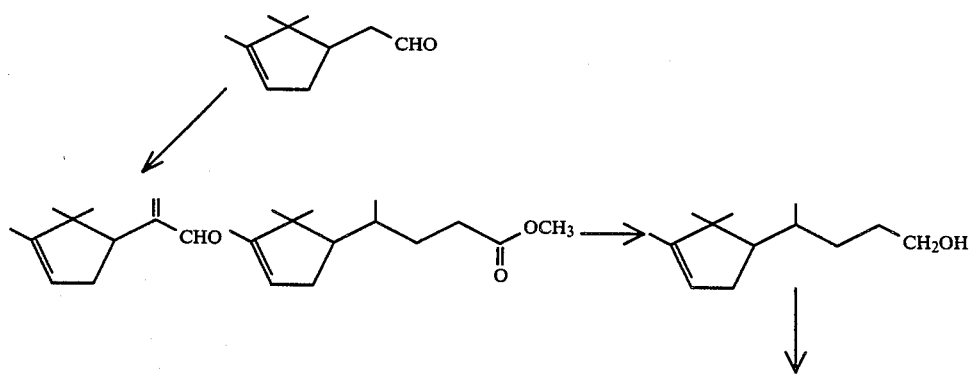

-continued
Scheme 5

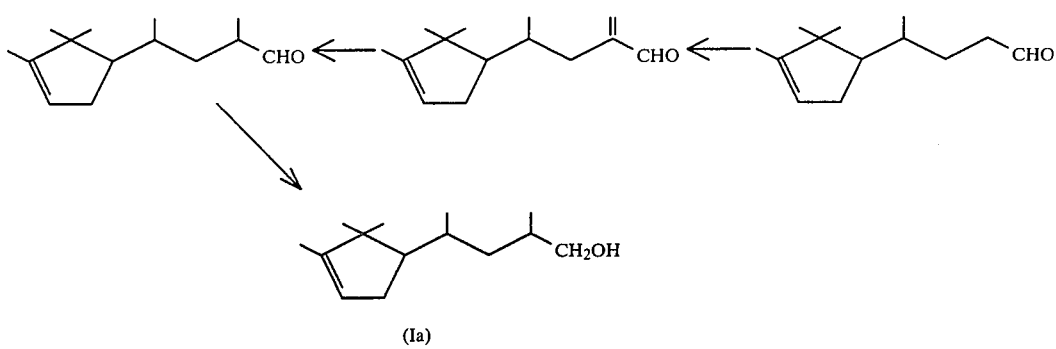

(Ia)

It is known that campholenic aldehyde can occur in optically active form or in any mixture of its antipodes as a function of the particular isomerism of the α-pinene used as starting material for its preparation. This implies that the products obtained from the processes illustrated by above given schemes 1 to 5 can occur also in different isomeric forms. We have noticed that with regard to their olfactive properties, the different diastereomers behave in a similar way. Consequently, whenever mention is made in the present description to a compound of formula (I), it is deemed to refer indifferrently to any of its diastereomers or to any mixture thereof.

The specific synthetic methods followed for the preparation of the compounds of the invention are based on the application of conventional discreet reaction steps. The details of these processes are given in the examples which follow. Modifications of reagents or reaction conditions over the ones given in the examples are possible, the originality of the described process residing in the specific choice of the different reaction steps and of the reaction sequence adopted.

The invention is better illustrated by the following examples wherein the temperatures are indicated in degrees centigrade and the abbreviations have the meaning common in the art.

EXAMPLE 1

Preparation of (−)-(E)-3,3-dimethyl-5-(2′,2′,3′-trimethyl-3′-cyclopenten-1′-yl)-4-penten-2-ol A solution of 22.0 g (0.1 M) of 3,3-dimethyl-5-(2,2,3-trimethyl-3-cyclopenten-1-yl)-4-penten-2-one in 50 ml of ethanol has been added dropwise to a mixture of 2.85 g (75 mM) of sodium borohydride in 100 ml of ethanol. The reaction is slightly exothermic and the temperature of the reaction mixture was kept below 32° by external cooling. The mixture was then kept under stirring overnight at room temperature and the excess of ethanol was evaporated under reduced pressure. The obtained residue was diluted with ether, washed with water until neutrality, dried and concentrated to give 23.7 g of a raw product which upon fractional distillation gave 21.5 g of (−)-(E)-3,3-dimethyl-5-(2′,2′,3′-trimethyl-3′-cyclopenten-1′-yl)-4-penten-2-ol (yield 97%).

$[\alpha]_D^{20} = -11.8°$;
IR: 3400 cm$^{-1}$;
NMR (60 MHz; CDCl$_3$): 0.78 and 0.98 (6H, 2s); 1.02 (6H, s); 1.14 (3H, d, J=3 Hz); 1.65 (3H, m); 3.35–3.68 (1H, m); 5.25 (1H,m); 5.38–5.55 (2H, m) δ ppm;
MS: M$^+$:220(0.1); m/e:204(1), 189(1), 178(21), 163(12), 149(7), 135(11), 121(34), 109(64), 91(15), 79(11), 69(100), 55(11), 41(27)

3,3-Dimethyl-5-(2,2,3-trimethyl-3-cyclopenten-1-yl)-4-penten-2-one used as starting material in the above described process can be prepared as follows.

a. (+)-(E)-3-Methyl-5-(2′,2′,3′-trimethyl-3′-cyclopenten-1′-yl)-3-penten-2-one

152 G (1.0 M) of campholenic aldehyde having a purity of about 75% were added dropwise under stirring in 15–20 minutes to a mixture cooled at −5/−10° of 400 g (6.1 M) of methyl-ethyl ketone, 1025 g (35 M) of methanol, 30.5 g (0.54 M) of potassium hydroxide and 380 g of water. The mixture was kept at −5° for 24 hours, then at room temperature for the same period and neutralized thereupon with H$_2$SO$_4$ to 62.5%. After concentration under reduced pressure, the obtained residue was dissolved in 200 ml of water, diluted with petrol ether 30/50, washed until neutrality, dried and concentrated. 189.3 G of a raw material was thus obtained which on distillation with a Vigreux column of 15 cm length gave 144.6 g of (E)-3-methyl-5-(2,2,3-trimethyl-3-cyclopenten-1-yl)-3-penten-2-one having a purity of 86% (yield 60.4%).

$[\alpha]_D^{20} = +2.2°$; Bp. 67°/6.65 Pa;
IR: 1670 cm$^{-1}$;
NMR (60 MHz; CDCl$_3$): 0.82 and 1.0 (6H, 2s); 1.65 (3H, s); 1.8 (3H, s); 2.28 (3H, s); 5.22 (1H, m); 6.56–6.83 (1H, m) δ ppm;
MS: M$^+$=206(7); m/e:191(16), 173(17), 158(6), 145(7), 136(39), 121(26), 109(49), 98(72), 93(67), 79(36), 67(61), 55(32), 43(100).

b. (−)-(E)-3,3-Dimethyl-5-(2′,2′,3′-trimethyl-3′-cyclopenten-1′-yl)-4-penten-2-one In a flask containing a solution of 45 g of NaOH in 45 ml of water, there were added under nitrogen atmosphere and at room temperature 0.8 g of hexadecyltrimethylammonium bromide and in one portion 10.3 g (50 mM) of the ketone obtained according to par. a. above a purity of 89% in 10 ml of toluene. The reaction mixture was vigorously stirred while a flow of methyl chloride was introduced. After about 9 hours, one could observe the complete disappearance of the starting ketone. The mixture was poured onto ice, extracted twice with ether and the organic extracts were washed until neutrality, dried, concentrated and distilled by means of a bulb apparatus (13.3 Pa). 9.3 G of the desired ketone having a purity of 92% (yield 87.4%) were obtained.

$[\alpha]_D^{20} = -19.5°$; Bp. 50°/6.65 Pa;
IR: 1720 cm$^{-1}$;
NMR (60 MHz; (CDCl$_3$): 0.78 and 0.99 (6H, 2s); 1.22 (6H, s); 1.65 (3H, s); 2.11 (3H, s); 5.12 (1H, m); 5.5–5.63 (2H, m) δ ppm;

MS: M+=220(4); m/e:177(25), 162(2), 149(5), 135(5), 121(27), 109(53), 91(12), 69(100), 55(12), 41(22).

EXAMPLE 2

Preparation of
(−)-(E)-3,3-dimethyl-5-(2',2',3'-trimethyl-3'-cyclopenten-1'-yl)-4-penten-2-ol a. A mixture of 456 g (3 M) of campholenic aldehyde having a purity of 75% and 348 g (6 M) of propionic aldehyde was added dropwise to a refluxing solution of 18 ml of sodium hydroxide at 30% in 800 ml of methanol. After termination of the addition, the reaction mixture was maintained at reflux for 2 hours, then after having been cooled to room temperature it was poured into 1000 ml of water. The product was extracted with three fractions of 300 ml each of petrol ether 30/50 and the organic extracts were washed with water then with an aqueous NaCl solution until neutrality, dried and concentrated. The residue was distilled over a Vigreux column of 10 cm length and gave 323 g of (+)-(E)-2-methyl-4-(2,',2',3'-trimethyl-3'-cyclopenten-1'-yl)-2-butenal (yield 56%).

$[\alpha]_D^{20} = +1.2°$; Bp. 57°/9.21 Pa;
IR: 2735 and 1740 cm$^{-1}$;
NMR (60 MHz ; CDCl$_3$): 0.82 and 1.2 (6H, 2s); 1.65 (3H, m); 1.75 (3H, s); 5.22 (1H, m); 6.52 (1H, t, J=6 Hz); 9.4 (1H, s) δ ppm
MS : M+=192(9); m/e: 177(5), 164(1), 159(16), 149(17), 121(40), 108(100), 93(88), 79(43), 67(49), 55(37), 41(48).

b. 19.2 g (0.1 M) of the aldehyde prepared according top letter a. above were added dropwise to a solution of 13.4 g (0.12 M) of potassium tert-butoxide in 100 ml of tert-butanol at 30°. The introduction took approx. 10 minutes and the mixture was kept at room temperature for ½ hour, then it was cooled to 5°. At this temperature, 17 g (0.12 M) of methyl iodide were added dropwise and the mixture was stirred for 10 minutes at 5° whereupon the temperature was allowed to raise to room temperature. The mixture was poured onto icy water and extracted with petrol ether 30/50 and the organic extracts were washed until neutrality dried and concentrated. On distillation, the residue gave on a bulb to bulb apparatus (6.65 Pa) 15.4 g of (−)-(E)-2,2-dimethyl-4-(2',2',3'-trimethyl-3'-cyclopenten-1'-yl)-3-butenal (yield 75%).

$[\alpha]_D^{20} = -16.1°$.
IR: 1740 and 2740 cm$^{-1}$;
NMR (60 MHz; CDCl$_3$): 0.73 and 0.97 (6H, 2s); 1.18 (6H, s); 1.65 (3H, m); 5.25 (1H, m); 5.37–5.56 (2H, m); 9.32 (1H, s) δ ppm;
MS : M+=206(8) ; m/e 191(2), 177(24), 163(3), 149(5), 134(13), 121(28), 109(47), 91(18), 79(13), 69(100), 55(12), 41(32).

c. 3.09 G (15 mM) of the aldehyde obtained according to letter b. above in 15 ml of anhydrous ether were added to a solution of magnesium methyl iodide (prepared from 2.6 g of methyl iodide and 0.43 g of magnesium turnings in ether).

The reaction mixture was kept under stirring at room temperature for 3 hours, then it was poured into a saturated icy solution of NH$_4$Cl. After extraction with ether and washing of the ethereal extracts with H$_2$O/NaCl until neutrality, drying and concentration, 3.15 g of (−)-(E)-3,3-dimethyl-5-(2',2',3'-trimethyl-3'-cyclopenten-1'-yl)-4-penten-2-ol (yield 95%) were obtained on a bulb to bulb distillation.

The analytical characters of the obtained product were in all respects identical to those of a sample prepared according to the previous example.

EXAMPLE 3

(−)-(1'S,E)-3-Ethyl-3-methyl-5-(2',2',3'-trimethyl-3'-cyclopenten-1'-yl)-4-penten-2-ol This compound was prepared according to the process described in Example 1 by reduction by means of sodium borohydride of (−)-(1'S,E)-3-ethyl-3-methyl-5-(2',2',3'-trimethyl-3'-cyclopenten-1'-yl)-4-penten-2-one with a yield of 97%.

$[\alpha]_D^{20} = -9.9°$;
IR: 3400 cm$^{-1}$;
NRM: 0.72 and 0.92 (9H, 2s); 0.9 (3H, t, J=7 Hz); 1.62 (3H, s); 5.22 (1H, m); 5.2–5.51 (2H, m) δ ppm;
MS: M+=236(0.1); m/e: 203(2), 192(32), 177(9), 163(6), 149(6), 135(14), 121(57), 109(100), 91(26), 83(92), 79(20), 67(21), 55(64), 42(27).

(1'S,E)-3-Ethyl-3-methyl-5-(2',2',3'-trimethyl-3'-cyclopenten-1'-yl)-4-penten-2-one, used as starting material in the process described above, can be obtained by ethylation of (+)-(E)-3-methyl-5-(2',2',3'-trimethyl-3'-cyclopenten-1'-yl)-3-penten-2-one (see Example 1a.) with ethyl bromide according to the following procedure. 0.1 M of the pentenone was introduced dropwise into a flask containing a solution of 13.4 g (0.12 M) of potassium tert-butoxide in 100 ml of tert-butoxide in 100 ml of tert-butanol at 30° (introduction period: 10 minutes). The mixture was kept under stirring for 30 minutes at 30°, then it was cooled to about 5° and at that temperature 0.12 M of the chosen alkyl halide were introduced dropwise and the obtained mixture was kept under stirring at that temperature for 10 minutes, whereupon it was brought to room temperature. The mixture was then poured onto ice water, extracted with petrol ether 30/50 and the organic extracts were washed, dried and concentrated. The desired product was obtained by distillation under vacuum.

$[\alpha]_D^{20} = -8.9°$; yield 32.5%
IR: 1700 cm$^{-1}$;
NMR (60 MHz; CDCl$_3$): 0.72 and 0.97 (6H, 2s); 1.17 (3H, s); 0.82 (3H, t, J=7 Hz); 1.63 (3H, s); 2.08 (3H, s); 5.23 (1H, m); 5.45–5.62 (2H, m) δ ppm;
MS: M+=234(4); m/e: 205(1), 191(42), 175(1), 163(3), 149(3), 135(10), 126(13), 121(42), 109(70), 91(15), 83(100), 79(12), 55(70), 43(29).

EXAMPLE 4

(+)-(1'S)-2-Methyl-4-(2',2',3'-trimethyl-3'-cyclopenten-1'-yl)-1-pentanol

For the preparation of this compound, the following general method was applied. In a reaction vessel equipped with a condenser, a thermometer and a dropping funnel, there were placed 0.76 g (0.02 M) of LiAlH$_4$ in 50 ml of anhydrous either and there were introduced dropwise 0.04 M of (−)-(1'S)-2-methyl-4-(2',2',3'-trimethyl-3'-cyclopenten-1'-yl)-pentanal in solution in 80 ml of anhydrous ether while refluxing. The reaction mixture was then stirred at room temperature for 2 hours. 1.52 Ml of water, 1.52 ml of NaOH at 15% and 4.56 ml of water were successively added thereto. After filtration, a clear filtrate was evaporated under vacuum and the obtained residue was bulb distilled to give the desired pentanol (150°/13.3 Pa; yield 94%).

[α]$_D^{20}$= +5.9°;
IR: 3350 cm$^{-1}$;
NMR (60 MHz; CDCl$_3$): 0.78–1.15 (12H, m); 1.51–1.69(3H, m); 3.22–3.62 (2H, m); 5.1–5.3 (1H, m) δ ppm;
MS: M+ =210(14); m/e: 195(45), 177(10), 135(18), 121(55), 109(70), 99(65), 95(100), 91(22), 81(36), 67(42), 55(41), 41(35).

The starting pentanal can be prepared as follows:

a. 1 M of (−)-(1'S)-2-[2-(2',2',3'-trimethyl-3'-cyclopenten-1'-yl)-propyl]-2-propenal, see b. above, was hydrogenated in 1.5 l of ethanol in the presence of 4 g of Raney-nickel at room temperature and atmospheric pressue. After absorption of one equivalent of H$_2$ the reaction was stopped, and the mixture filtered, washed, concentrated and distilled. The aldehyde obtained with a yield of 96.5% possessed the following analytical characters:
[α]$_D^{20}$=2.5°;
IR: 1730 cm$^{-1}$;
NMR (60 MHz, CDCl$_3$): 0.75–1.2 (12H, m); 1.5–1.7 (3H, m); 5.1–5.25 (1H, m); 9.47–9.66 (1H, m) δ ppm;
MS: M+ =208(22); m/e: 193(28), 175(68), 166(11), 149(10), 135(82), 119(50), 109(100), 99(38), 91(42), 81(59), 67(68), 55(46), 43(73).

b. (−)-(1'S)-2-[2-(2',2',3'-trimethyl-3'-cyclopenten-1'-yl)-propyl]-2-propenal was prepared by treating (−)-(1+S)-4-(2',2',3'-trimethyl-3'-cyclopenten-1'-yl)-pentanal—see c. hereinbelow—with formaldehyde. 9 G (46 mM) of said pentanal were heated to reflux with 15 g (46 mM) of formaldehyde (30% solution, origin: Fluka AG) in a three-necked reaction vessel equipped with a condesner, a thermometer, a stirrer and a dropping funnel. The operation was carried out under a nitrogen atmosphere. While keeping at reflux, there were then added rapidly 0.968 g (7.5 mM) of dibutylamine. After having been left for 3 hours at reflux, the mixture was cooled and the organic phase was decanted, separated and distilled. The desired propenal was obtained under the form of a diastereoisomeric mixture (20/80): 7.89 g of a colorless oil; Bp. 73°/20 Pa; yield 83%.
[α]$_D^{20}$=11.7°;
IR: 1695 cm$^{-1}$;
NMR (60 MHz; CDCl$_3$): 0.75–1.0 (3H, m); 0.88 and 1.5 (6H, 2d); 1.48–1.58 (3H, m); 5.11–5.3 (1H, m); 6.02–6.2 (2H, 2s); 9.03 (1H, 1s) δ ppm;
MS: M+ =206(13); m/e: 191(8), 173(17), 158(5), 145(5), 135(50), 131(12), 121(31), 109(100), 95(47), 91(26), 79(28), 67(30), 55(22), 41(39).

c. (−)-(1S)-4-(2',2',3'-trimethyl-3'-cyclopenten-1'-yl)-pentanal was prepared by oxidation of (−)-(1'S)-4-(2',2',3'-trimethyl-3'-cyclopenten-1'-pentanol, see d. hereinbelow, by means of pyridinium chlorochromate. A solution of the alcohol (0.66 M) in 15 ml of anhydrous CH$_2$Cl$_2$ was added to a suspension of 22.8 g (0.016 M) of pyridinium chlorochromate in 150 ml of methylene chloride. After having been left at room temperature for 1 h ½ hours, the reaction mixture was filtered over a column filled with SiO$_2$. After concentration at reduced pressure, the residue formed was distilled to give the desired aldehyde.
Bp. 65°/13.1 Pa; yield 75%;
[α]$_D^{20}$=3.8°;
IR: 1720 cm$^{-1}$;
NMR (60 MHz; CDCl$_3$): 0.9 and 1.09 (6H, 2s); 0.85–1.2 (3H, m); 1.55–1.7 (3H, m); 5.12–5.3 (1H, m); 9.71–9.88 (1H, m) δ ppm;

The product occurred under the form of two diastereomers;
(20%) A: MS: M+ =194(35); m/e: 179(29), 161(100), 151(8), 145(2), 135(80), 119(80), 109(62), 95(59), 85(27), 81(41), 67(59), 55(32), 41(45).
(80%) B: MS: M+ =194(23); m/e: 179(25), 161(100), 151(8), 135(58), 119(79), 109(71), 95(62), 91(34), 84(42), 81(49), 67(69), 55(40), 41(50).

d. (−)-(1'S)-4-(2',2',3'-trimethyl-3'-cyclopenten-1'-yl)-1-pentanol has been prepared starting from methyl (−)-(1'S)-4-(2',2',3'-trimethyl-3'-cyclopenten-1'-yl)-pentanoate, see e. hereinbelow, as follows.

0.04 M of the ester to be reduced in solution in 80 ml of anhydrous ether were added dropwise to a suspension of LiAlH$_4$ (0.04 M; 1.52 g) in 100 ml of anhydrous ether while refluxing. After having left the mixture under stirring at room temperature for 2 hours, there were added thereto successively and with precaution 1.52 ml of water, 1.52 ml of NaOH at 15% and 4.56 ml of water. After filtration, the excess of solvent was evaporated under vacuum and the residue was distilled. The obtained pentanol occurred under the form of a diastereomeric mixture having Bp. 78°/6.65 Pa; yield 98%.
[α]$_D^{20}$=4.2°;
IR: 3320 cm$^{-1}$;
NMR (60 MHz; CDCl$_3$): 0.85–1.12 (9H, m); 1.58–1.63 (3H, m); 3.61 (2H, t, J=6 Hz); 5.12–5.29 (1H, m) δ ppm;
20% diastereomer A: MS: M+ =196(16); m/e: 181(100), 163(23), 152(2), 135(16), 121(45), 109(68), 95(97), 85(53), 81(48), 69(61), 61(1), 55(28), 41(59).
80% diastereomer B: MS: M+ =196(15); m/e: 181(65), 163(21), 153(4), 137(15), 121(38), 109(68), 95(100), 85(49), 81(41), 69(53), 55(25), 41(41).

e. Methyl (−)-(1'S)-4-(2',2',3'-trimethyl-3'-cyclopenten)-pentanoate has been prepared starting from (−)-(1'R)-2-(2',2',3'-trimethyl-3'-cyclopenten-1'-yl)-2-propenal, see f. hereinbelow, as follows.

1 M of said propenal was hydrogenated in 1.5 l of ethanol in the presence of 4 g of Raney-nickel at room temperature and at atmospheric pressure. After absorption of one equivalent of hydrogen, the reaction was stopped and the mixture was filtered, concentrated and distilled to give (−)-(1'S)-2-(2',2',3'-trimethyl-3'-cyclopenten-1'-yl)-propanal, in the form of a diastereomeric mixture (60/40), having Bp. 47°–52°/6.65 Pa, yield 85%.
[α]$_D^{20}$=5.1°;
IR: 1730 cm$^{-1}$;
NMR (60 MHz; CDCl$_3$): 0.82–1.22 (9H, m); 1.5–1.68 (3H, m); 5.1–5.3 (1H, m); 9.51–9.65 (1H, m) δ ppm;

218 g (1.2 M) of methyl dimethyl-phosphonoacetate have been slowly added to a mixture of 2000 ml of anhydrous isopropylether, 150 g of HMPT and 24 g (1 M) of sodium hydride kept under nitrogen atmosphere. The temperature of the reaction mixture was kept between 20° and 25° during the addition, as well as during the supplemental addition of 140 g (0.843 M) of the aldehyde obtained as described above dissolved in 125 ml of isopropylether. After having been heated at 70°–72° for 3 hours, the reaction mixture was cooled to room temperature and the excess sodium hydride decomposed by addition of methanol. After extraction with ether, washing and drying of the organic phase, followed by evaporation of the volatiles, 135 g of methyl (+)-(1'S)-4-(2',2',3'-trimethyl-3'-cyclopenten-1'-yl)-2-pentenoate were obtained with a yield of about 65%. The product consisted of a diastereomeric mixture (20/80).

$[\alpha]_D^{20} = +1°$;

IR: 1720 cm$^{-1}$;

NMR (60 MHz; CDCl$_3$):0.88 and 1.08 (6H, 2s); 0.81–1.2 (3H, m); 3.69 (3H, s); 5.09–5.27 (1H, m); 5.75 and 5.79 (1H, 2d, J=16 Hz); 6.87 and 6.91 (1H, 2dxd, J=16 and 9 Hz) δ ppm;

The obtained pentenoate was reduced means of a catalytic halogenation in the presence of Raney-nickel according to the procedure above indicated for the reduction of (—)-(1'R)-2-(2',2',3'-trimethyl-3'-cyclopenten-1'-yl)-2-propenal.

Methyl (—)-(1'S)-4-(2',2',3'-trimethyl-3'-cyclopenten-1'-yl)-pentanoate presented the following analytical data: Bp. 56°/13.3 Pa;

$[\alpha]_D^{20} = -2.9°$;

IR: 1740 cm$^{-1}$;

NMR (60 MHz; CDCl$_3$): 0.82 and 1.05 (6H, 2s); 0.78–1.03 (3H, m); 1.5–1.65 (3H, m); 3.67 (3H, s); 5.05–5.25 (1H, m) δ ppm;

The product occurred in the form of a diastereomeric mixture (20/80).

A: M: M$^+$ =224(11); m/e: 209(100), 193(3), 177(50), 159(7), 149(18), 141(2), 135(63), 121(22), 115(15), 109(62), 95(33), 79(38), 73(15), 67(32), 55(32), 41(21).

B: MS: M$^+$ =224(18); m/e:209(100), 193(4), 177(61), 68(3), 159(8), 149(20), 135(81), 129(3), 121(29), 115(25), 109(98), 95(51), 91(31), 81(35), 73(22), 67(51), 59(21), 55(52), 41(36).

f. (—)-(1'R)-2-(2',2',3'-trimethyl-3'-cyclopenten-1'-yl)-2-propenal was prepared starting from campholenic aldehyde (purity 75%; $[\alpha]_D^{20} = +2.2°$) according to the following procedure: a mixture of 500 g (3.3 M) of campholenic aldehyde and 333 g (3.3 M) of formaldehyde (30% solution; origin Fluka AG) was refluxed under nitrogen atmosphere. 20 g (0.155 M) of dibutylamine were then added rapidly to the mixture while keeping the reflux. The reaction mixture was thus heated for 3 hours, then the organic phase was decanted and distilled to give 421.2 of the desired propenal having Bp. 65°–70°/4×10$^2$ Pa (purity 80%); yield 62.4%.

$[\alpha]_D^{20} = -75°$

IR: 1700 cm$^{-1}$;

NMR (60 MHz; CDCl$_3$): 0.69 and 1.02 (6H, 2s); 1.55–1.7 (3H, m); 2.15–2.5 (2H, m); 3.2 (1H, t, J=8 Hz); 5.18–5.4 (1H, m); 6.1 and 6.32 (2H, 2s); 9.55 (1H, s) δ ppm;

MS: M$^+$ =164(41); m/e: 149(75), 146(4), 135(27), 131(34), 121(66), 115(9), 107(95), 93(100), 79(71), 67(39), 53(42), 41(87).

EXAMPLE 5

Preparation of (—)-(1'R)-2-methyl-4-(2',2',3'-trimethyl-3'-cyclopenten-1'-yl)-4-hexene-1-ol This compound was prepared by reduction by means LiAlH$_4$ of ethyl (—)-(1'R)-2-methyl-4-(2',2',3'-trimethyl-3'-cyclopenten-1'-yl)-4-hexenoate according to the method described in Example 4, paragraph d.

The desired alcohol was obtained in the form of an isomeric mixture with a yield of 95%.

$[\alpha]_D^{20} = -60.2°$;

IR: 3350 cm$^{-1}$;

NMR (60 MHz; CDCl$_3$): 0.7–1.12 (9H, m); 1.52–1.78 (6H, m) 3.31–3.62 (2H, m); 5.19–5.65 (2H, m) δ ppm;

MS: M$^+$ =222(43); m/e: 207(17), 193(10), 189(5), 175(5), 163(18), 149(47), 135(20), 121(100), 107(68), 93(76), 79(45), 67(39), 55(70), 41(93).

The ester using as starting material in the said process can be obtained as follows:

a. Ethyl (—)-(1'R)-2-methyl-4-(2',2',3'-trimethyl-3'-cyclopenten-1'-yl)-4-hexenoate was prepared starting from 0.3 M of (—)-(1'R)-3-(2',2',3'-trimethyl-3'-cyclopenten-1'-yl)-3-buten-2-ol, see b. hereinbelow, and 0.9 M of ethyl ortho-propionate. The mixture of the two reactants was heated to 120° and 3 g of pivalic acid in 30 g of ortho-propionate were added to the mixture;after 3 hours, about 50 ml of ethanol were recovered by direct evaporation of the mixture. After cooling, the mixture was distilled under reduced pressure to give the desired ester having Bp. 98°/6.65 Pa (yield 96%).

$[\alpha]_D^{20} = -36.3°$;

IR: 1740 cm$^{-1}$;

NMR (60 MHz; CDCl$_3$); CDCL$_3$): 0.68–1.4 (12H, m); 1.52–1.8 (6H, m); 1.8–3.21 (6H, m); 3.5 (2H, q, J=7 Hz); 4.1 (2H, q, J=7 Hz); 5.20–5.33 (1H, m); 5.38 (1H, q, J=7 Hz) δ ppm;

MS: M$^+$ =264(64); m/e: 249(29), 235(52), 219(7), 208(28), 189(8), 175(42), 164(44), 149(66), 133(45), 119(61, 107(63), 91(64), 79(39), 67(31), 55(58), 41(100).

b. (—)-(1'R)-3-(2',2',3'-trimethyl-3'-cyclopenten-1'-yl)-3-buten-2-ol was prepared starting from (—)-(1'R)-2-(2',2',3'-trimethyl-3'-cyclopenten-1'-yl)-2-propenal—see Example 4, f.-by a Grignard reaction by means of methyl iodide. The desired alcohol was obtained with a yield of 85%.

$[\alpha]_D^{20} = -32°$;

IR: 3350 cm$^{-1}$;

NMR (60 MHz; CDCl$_3$): 0.79 and 0.81 (3H, 2s); 1.07 (3H, s); 1.31 and 1.34 (3H, 2d, J=6 Hz); 1.58–1.72 (3H, m); 4.29 (1H, q, J=7 Hz); 4.93–5.02 (1H, m); 5.20–5.40 (2H, m) δ ppm;

MS: M$^+$ =180(8); m/e: 162(17), 147(65), 137(6), 133(22, 119(100), 105(82), 99(22), 91(78), 79(50), 67(41), 55(40), 43(69).

EXAMPLE 6

Preparation of (—)-(1'S)-2-methyl-4-(2',2',3'-trimethyl-3'-cyclopenten-1'-yl)-4-penten-1-ol A solution of 53 g (0.212 M) of ethyl (—)-(1'S)-2-methyl-4-(2',2',3'-trimethyl-3'-cyclopenten-1'-yl)-4-pentenoate—see a. hereinbelow—in 200 ml of anhydrous ether was added dropwise with vigorous stirring and under nitrogen atmosphere to a suspension of 7.6 g of LiAlH$_4$ (0.2 M) in 300 ml of anhydrous ether while keeping the reflux. Once the addition was over, the reaction mixture was kept under stirring at room temperature, then there was added successively with precaution: 7.6 ml of water, 7.6 ml of a 15% solution of NaOH and 22.8 ml of water. After filtration, the solvent was evaporated under vacuum and the residue was distilled to give 43.1 g of a colorless oil having Bp. 76°/20 Pa (yield 97.7%).

$[\alpha]_D^{20} = -52.7°$;

IR: 3330 cm$^{-1}$;

NMR (60 MHz; CDCL$_3$): 0.75 and 1.09 (6H, 2s); 0.8–1.1 (3H, m); 1.52–1.69 (3H, m); 1.7–2.8 (6H, m); 3.31–3.62 (2H, m); 4.91 (2H, s); 5.18–5.35 (1H, m) δ ppm;

The product occurred in the form of a diastereomeric mixture:

A: MS: M+=208(53); m/e: 193(36), 175(12), 161(3), 149(20), 135(85), 119(38), 107(100), 91(87), 79(40), 67(35), 55(31), 41(75).

B: MS: M+=208(50); m/e: 193(32), 175(12), 149(18), 135(86), 119(41), 107(100), 99(15), 91(72), 79(46), 67(25), 55(32), 41(83).

a. Ethyl (−)-(1′S)-2-methyl-4-(2′,2′,3′-trimethyl-3′-cyclopenten-1′-yl)-4-pentenoate was prepared starting from (−)-(1′R)-2-(2′,2′,3′-trimethyl-3′-cyclopenten-1′-yl)-2-propen-1-ol—see b. hereinbelow—as follows. 55 G of said alcohol 0.33 M and 158 g (0.9 M) of ethyl ortho-propionate were heated to 120°, and 3 g of pivalic acid in solution in 20 ml of ethyl ortho-propionate were introduced thereto. The ethanol formed (about 50 ml) was evaporated during its formation (2½ h). After cooling, the excess ethyl ortho-propionate was taken off under vacuum and the residue distilled.

Bp. 74°–76°/4 Pa; yield 94%;
$[\alpha]_D^{20} = -46.2°$;
IR: 1740 cm$^{-1}$;
NMR (60 MHz; CDCl$_3$): 0.75 and 1.08 (6H, 2s); 1.1–1.4 (6H, m); 1.56–1.70 (3H, m); 1.9–3.8 (6H, m); 4.11 (2H, q, J=7 Hz); 4.87 (2H, s); 5.18–5.32 (1H, m) δ ppm;
MS: M+=250(43); m/e: 235(40), 221(1), 205(4), 189(20), 176(8), 161(53), 149(38), 135(100), 121(33), 107(51), 91(43), 79(39), 67(17), 55(27), 41(52).

b. (−)-(1′R)-2-(2′,2′,3′-trimethyl-3′-cyclopenten-1′-yl)-2-propen-1-ol was prepared starting from (−)-(1′R)-2-(2′,2′,3′-trimethyl-3′-cyclopenten-1′-yl)-2-propen-1-al—see Example 4, f.—. A solution of 284 g (1.73 M) of said aldehyde (purity 80%) in 0.9 l of anhydrous ether was added dropwise to a suspension kept under stirring and nitrogen atmosphere of 26.2 g (0.69 M) of LiAl H$_4$ in 1.8 l of anhydrous ether while keeping the temperature of the mixture at 0°–5° (time: 4 hours). The mixture was kept at 0° during 2 hours under stirring whereupon the following fractions were successively added thereto: 26.2 ml of water, 26.2 ml of a 15% solution of NaOH and 78.6 ml of water. After one hour, the mixture was filtered, concentrated in vacuum and the obtained residue distilled. 286 G of a colorless oil were thus obtained having 80% purity.

$[\alpha]_D^{20} = -56°$; yield 99%;
IR: 333 cm$^{-1}$;
NMR (60 MHz; CDCl$_3$); 0.74 and 1.04 (6H, 2s); 1.5–1.62 (3H, m); 2.1–2.76 (3H, m); 3.95–4.2 (2H, m); 4.9–5.0 (1H, m); 5.15–5.35 (2H, m) δ ppm;
MS: M+=166(33); m/e: 151(7), 148(18), 133(100), 123(14), 119(18), 108(46), 105(82), 99(4), 91(74), 79(52), 67(35), 55(26), 41(42).

EXAMPLE 7

Preparation of (−)-(/′S,E)-2-ethyl-2-methyl-4-(2′,2′,3′-trimethyl-3′-cyclopenten-1′-yl)-3-buten-1-ol This alcohol was prepared by reducing with sodium borohydride the corresponding aldehyde. 0.1 M of (−)-(E)-2-ethyl-2-methyl-4-(2′,2′,3′-trimethyl-3′-cyclopenten-1′-yl)-3-buten-1-al—see a. hereinbelow—was added dropwise to a solution of 2.85 g (75 mM) of NaBH$_4$ in 100 ml of ethanol by taking care that the temperature of the mixture does not raise beyond 32°. The mixture was kept at room temperature overnight under stirring, then the ethanol was evaporated in vacuum. The residue was diluted with ether, washed until neutrality, dried and concentrated. On distillation, the residue gave the desired alcohol with a yield of 95%.

$[\alpha]_D^{20} = -11.1°$;
IR: 3350 cm$^{-1}$;
NMR (60 MHz; CDCl$_3$): 0.72, 0.96 and 0.98 (9H, 3s); 0.82 (3H, t, J=6 Hz); 1.63 (3H, s); 3.31 (2H, d, J=6 Hz); 5.22 (1H, m); 5.28–5.49 (2H, m) δ ppm;
MS: M+=222(6); m/e: 207(1), 191(53), 161(3), 152(14), 135(18), 21(57), 109(95), 97(28), 83(100), 79(23), 67(21), 55(88), 41(35).

a. (−)-(E)-2-ethyl-2-methyl-4-(2′,2′,3′-trimethyl-3′-cyclopenten-1′-yl)-3-buten-1-al was prepared by methylating (−)-(E)-2-ethyl-4-(2′,2′,3′-trimethyl-3′-cyclopenten-1′-yl)-2-buten-1-al, see b. hereinbelow, according to the alkylation procedure indicated in Example 1, b. Yield 83.6%.

$[\alpha]_D^{20} = -8.5°$;
IR: 2700, 1710 cm$^{-1}$;
NMR (60 MHz; CDCl$_3$): 0.72 and 0.97 (6H, 2s); 1.14 (3H, s); 1.62 (3H, s); 5.21 (1H, m); 5.35–5.59 (2H, m); 9.33 (1H, s) δ ppm;
MS: M+=220(9); m/e: 205(1), 191(50), 163(4), 149(5), 135(13), 121(48), 109(72), 91(26), 83(100), 79(19), 67(17), 55(76), 41(30).

b. (−)-(E)-2-ethyl-4-(2′,2′,3′-trimethyl-3′-cyclopenten-1′-yl)-3-buten-1-al was prepared starting from campholenic aldehyde as follows:

A mixture of 76 g (0.5 M) of (+)-campholenic aldehyde (purity 75%) and 72 g (1 M) of freshly distilled butanol were added dropwise to a refluxing mixture of 3 ml of 40% NaOH in 100 ml of methanol. The introduction time was of about 30 min. The reaction mixture was kept at reflux for 2 hours, then it was allowed to reach room temperature and poured into 350 ml of water and extracted with 3 fractions of 200 ml each of 30/50 petrol ether. The organic extracts were washed until neutrality, dried and concentrated to give a residue which on distillation with a Vigreux column gave 50.6 g (yield 49%) of the desired aldehyde. Bp. 61°/6.65 Pa.

$[\alpha]_D^{20} = -1.4°$;
IR: 2750, 1700 cm$^{-1}$;
NMR (60 MHz; CDCl$_3$): 0.83 and 1.01 (6H, 2s); 1.03 (3H, t, J=7 Hz); 1.65 (3H, s); 5.23 (1H, m); 6.47 (1H, t, J=7 Hz); 9.38 (1H, s) δ ppm;
MS: M+206(9); m/e: 191(4), 177(3), 173(8), 163(14), 136(22), 121(40), 108(100), 93(80), 79(39), 67(43), 55(25), 41(52).

EXAMPLE 8

Preparation of (−)-(1′S,E)-2,2-dimethyl-4-(2′,2′,3′-trimethyl-3′-cyclopenten-1′-yl)-3-buten-1-ol This compound was obtained according to the method described in Example 7 starting from (E)-2,2-dimethyl-4-(2′,2′,3′-trimethyl-3′-cyclopenten-1′-yl)-3-buten-1-al, which compound was prepared from (E)-2-methyl-4-(2′,2′,3′-trimethyl-3′-cyclopenten-1′-yl)-2-buten-1-al.

The desired compound showed the following analytical characters:

$[\alpha]_D^{20} = -13.2°$;
IR: 3350 and 970 cm$^{-1}$;
NMR (60 MHz; CDCl$_3$): 0.72 and 0.93 (6H, 2s); 1.0 (6H, s); 1.62 (3H, broad s); 3.3 (2H, d); 5.22 (1H, m); 5.31–5.52 (2H, m) δ ppm;
MS: M+=208(4); m/e: 193(3), 177(28), 161(2), 149(6), 138(19), 121(42), 109(57), 98(6), 93(24), 79(15), 69(100), 55(15), 41(28).

EXAMPLE 9

Preparation of
(−)-(1′S)-2-ethyl-2-methyl-4-(2′,2′,3′-trimethyl-3′-cyclopenten-1′-yl)-1-butanol This compound was prepared by reducing the corresponding butanal with NaBH$_4$ (see method of Example 7).

$[\alpha]_D^{20} = -5.7°$;
IR: 3350 cm$^{-1}$;
NMR: 0.78 and 0.98 (6H, 2s); 0.86 (3H, s); 1.64 (3H, large s); 3.36 (2H, s); 5.25 (1H, m) δ ppm;
MS: M$^+$=224(9); m/e: 209(47), 191(26), 179(2), 149(7), 135(26), 121(76), 107(100), 95(75), 81(57), 67(56), 55(56), 41(32).

a. (−)-2-ethyl-2-methyl-4-(2′,2′,3′-trimethyl-3′-cyclopenten-1′-yl)-butanal, used as starting material in the process indicated above can be obtained by ethylation of (−)-2-methyl-4-(2′,2′,3′-trimethyl-3′-cyclopenten-1′-yl)-butanal with ethyl bromide.

$[\alpha]_D^{20} = -7.1°$;
IR: 2700 and 1730 cm$^{-1}$;
NMR (60 MHz; CDCl$_3$): 0.72 and 0.98 (6H, 2s); 1.02 (3H, s); 0.82 (3H, t); 1.63 (3H, broad s); 5.23 (1H, m); 9.47 (1H, s) δ ppm;
MS: M$^+$=222(18); m/e=207(4), 189(10), 179(16), 147(4), 135(30), 121(78), 109(110), 95(63), 81(26), 67(30), 55(32), 41(38).

b. (−)-2-methyl-4-(2′,2′,3′-trimethyl-3′-cyclopenten-1′-yl)-butanal was obtained by catalytic hydrogenation of (E)-2-methyl-4-(2′,2′,3′-trimethyl-3′-cyclopenten-1′-yl)-2-butenal—see Example 2, ξ a.—in the presence of Raney-nickel.

IR: 2700 and 1730 cm$^{-1}$;
NMR (60 MHz; CDCl$_3$): 0.78 and 0.98 (6H, 2s); 1.13 (3H, d); 1.65 (3H, broad s); 5.21 (1H, m); 9.6 (1H, m) δ ppm;
MS: M$^+$=194(25); m/e: 179(20), 161(48), 151(8), 135(9), 121(100), 109(54), 93(53), 79(28), 67(41), 55(21), 41(55).

EXAMPLE 10

Preparation of
(+)-2,2-dimethyl-4-(2′,2′,3′-trimethyl-3′-cyclopenten-1′-yl)-1-butanol This compound was obtained according to the general method indicated in Example 9 by reducing with NaBH$_4$ (+)-2,2-dimethyl-4-(2′,2′,3′-trimethyl-3′-cyclopenten-1′-yl)-butanal.

$[\alpha]_D^{20} = +7.8°$;
IR: 3350 cm$^{-1}$;
NMR: 0.72 and 0.88 (6H, 2s); 0.98 (6H, 2s); 1.64 (3H, broad s); 3.30 (2H, s); 5.22 (1H, m) δ ppm;
MS: M$^+$=210(21); m/e: 195(100), 177(27), 165(3), 149(4), 135(14), 121(60), 107(83), 99(18), 95(54), 79(38), 67(38), 55(49), 41(80).

EXAMPLE 11

Perfuming of soap

100 G of soap chips, obtained from a commercial non-perfumed sodium soap prepared with coconut oil and tallow oil, were mixed with 0.5 g of one of the compounds prepared according to Examples 1 to 10 until a homogenous mass resulted. The soap composition thus obtained possessed a woody, balsamic and sandalwood-like odor.

EXAMPLE 12

Perfuming of solid powder detergent

A solid powder detergent base was prepared by mixing the following ingredients (parts by weight):

| | |
|---|---|
| Sodium lin. alkyl-benzene sulphonate (chain length C$_{11-5}$) | 8.0 |
| Ethoxylated tallow alcohol (14EO) | 2.9 |
| Sodium soap (chain length C$_{12-16}$ 13–26%; C$_{18-22}$ 74–87%) | 3.5 |
| Sodium triphosphate | 43.8 |
| Sodium silicate | 7.5 |
| Magnesium silicate | 1.9 |
| Carboxymethylcellulose | 1.2 |
| Sodium EDTA | 0.2 |
| Sodium sulphate | 21.2 |
| Water | 9.8 |
| | 100.0 |

The addition to the base detergent of a sample of one of the products of Examples 1 to 10 at a concentration of 0.1% conferred thereto a distinct and elegant woody, sandalwood type odor character.

EXAMPLE 13

A fabric softener base was prepared by mixing the following ingredients (parts by weight):

| Ingredient | Parts by weight | Origin |
|---|---|---|
| Praepagen WK | 10.0 | Hoechst |
| Emulsifier 0120 | 0.5 | Zschimmer & Schwarz |
| Polyglycol 400 | 2.0 | Hoechst |
| Distilled water | 84.4 | |
| Dye: Brilliant Blau R 28032 aqueous sol. at 0.5% | 0.1 | Siegle |
| Sodium chloride in water at 10% | 0.7 | |
| Poromycen F 10 | 0.1 | Kraft |
| Isopropyl alcohol C+ | 2.0 | Shell |
| | 99.8 | |

The addition to a sample of the above indicated softener base of one of the products of Examples 1 to 10 at a concentration 0.2% by weight conferred thereto a very distinct woody, sandalwood type odor.

EXAMPLE 14

A base perfume composition of woody-animal type was prepared by mixing the following ingredients (parts by weight):

| | |
|---|---|
| Decanal 10%* | 10 |
| Undecylenic aldehyde 10%* | 40 |
| Dodecylenic aldehyde 10%* | 10 |
| Methylnonylacetal 10%* | 10 |
| Angelica root oil 10%* | 10 |
| Castoreum 10%* | 20 |
| Degreased natural civet 10%* | 10 |
| Galbanum resinoid | 10 |
| Jasmin absolute 50%* | 100 |
| Olibanum oil | 10 |
| Patchouli | 30 |
| Styralyl acetate | 15 |
| α-Isomethylionone | 95 |
| Coriander oil | 5 |
| Hydroxycitronellol | 65 |
| Cyclopentadecanolide 10%* | 50 |
| synth. Jasmin | 100 |
| synth. Bergamot | 100 |
| synth. Lemon | 40 |
| Oak moss absolute 50%* | 30 |
| synth. Neroli | 20 |

-continued

| | |
|---|---|
| Muscone 10%* | 50 |
| Coumarin | 50 |
| Ambrette musk | 10 |
| Musk ketone | 30 |
| Diethyl phthalate | 50 |
| Total | 970 |

*in diethyl phthalate

By adding to 98 g of the above described base 2 g of (−)-(1'S,E)-3-ethyl-3-methyl-5-(2',2',3'-trimethyl-3'-cyclopenten-1'-yl)-4-penten-2-ol, a novel composition resulted with a well perceptible sandalwood character. By substituting for said pentanol equivalent amounts of (−)-(1'S)-2-methyl-4-(2',2',3'-trimethyl-3'-cyclopenten-1'-yl)-4-penten-1-ol or of (E)-3,3-dimethyl-5-(2,2,3-trimethyl-3-chclopenten-1-yl)-4-penten-2-ol, there were obtained compositions with a similar odor character. Analogous effects were observed by replacing the said synthetic products of the invention by natural sandalwood oil. In this case however, the concentration of the oil had to be increased to 3%. On the other hand, by replacing the said synthetic product of the invention by an equivalent amount of (+)-(1'S)-2-methyl-4-(2',2',3'-trimethyl-3'-cyclopenten-1'-yl)-1-pentanol, a novel composition resulted with a woody, amber-like character.

EXAMPLE 15

A base perfume composition of flowery-woody type was prepared by mixing the following ingredients (parts by weight):

| | |
|---|---|
| p-Tert-butylcyclohexyl acetate | 150 |
| Cedrenol | 100 |
| Florida orange oil | 100 |
| Dihydroterpinyl acetate | 70 |
| α-Methylionone[1] | 60 |
| synth. Geranium oil | 50 |
| Lavender oil | 40 |
| Cedryl acetate | 40 |
| Mayol ®[1][2] | 40 |
| Hydroxycitronellal[1] | 40 |
| Musk ketone | 30 |
| Isoeugenol | 30 |
| Fixateur 404 10%[1][3]* | 30 |
| Myrcenyl acetate | 30 |
| Benzophenone | 20 |
| Amyl salicylate | 20 |
| TCD acetate[1][4] | 20 |
| Cyclohexylethyl acetate | 20 |
| Discolorized oak moss 50%* | 20 |
| synth. Neroli | 10 |
| Dihydromyrcenol | 10 |
| β-Damascenone 1%* | 10 |
| Bergamot oil without furocoumarin | 10 |
| Total | 950 |

*in ethyl alcohol 95%
[1]origin: Firmenich SA, Geneva
[2]Hydroxymethyl isopropyl cyclohexane
[3]Ambrox ® base
[4](Tricyclo[5.2.1.0$^{2,6}$]dec-4-yl)-methyl acetate The resulting base composition was utilized to prepare novel compositions. To this end, 5 g of the products indicated below were added to 95 g of the base composition and the resulting compositions were subjected to an odor evaluation by a panel of experts who had to express their view on the intrinsic quality of the odor, its analogy with natural sandalwood oil and its odor strength.

a. (−)-(1'S)-2-methyl-4-(2',2',3'-trimethyl-3'-cyclopenten-1'-yl)-4-penten-1-ol;
b. (E)-3,3-dimethyl-5-(2',2',3'-trimethyl-3'-cyclopenten-1'-yl)-4-penten-2-ol;
c. Bacdanol (IFF)
d. Sandalore (L. Givaudan)
e. Sandacore (Kao Soap)
f. Brahmanol (Dragoco)

By taking into account all these criteria of evaluation, 80% of the experts declare themselves in favour of (−)-(1'S)-2-methyl-4-(2',2',3'-trimethyl-3'-cyclopenten-1'-yl)-4-penten-1-ol whereas the remaining 20% shared their preference among one or another of compounds b. to f.

On the other hand, 60% of these experts ranged (E)-3,3-dimethyl-5-(2',2',3'-trimethyl-3'-cyclopenten-1'-yl)-4-penten-2-ol as their second best choice.

What we claim is:

1. A compound of formula

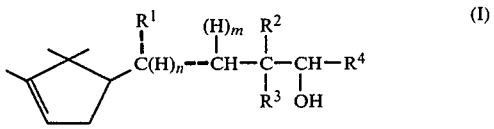

wherein:
a. $R^1=CH_3$; $n=m=1$; $R^2=CH_3$; $R^3=R^4=H$,
b. $R^1=CH_2$; $n=0$; $m=1$; $R^2=CH_3$; $R^3=R^4=H$,
c. $R^1=CH-CH_3$; $n=0$; $m=1$; $R^2=CH_3$; $R^3=R^4=H$,
d. $R^1=H$; $n=m=0$; $R^2=R^4=CH_3$; $R^3=C_2H_5$,
e. $R^1=H$; $n=m=0$; $R^2=R^3=R^4=CH_3$,
f. $R^1=H$; $n=m=0$; $R^2=CH_3$; $R^3=C_2H_5$; $R^4=H$,
g. $R^1=H$; $n=m=0$; $R^2=R^3=CH_3$; $R^4=H$,
h. $R^1=H$; $n=m=1$; $R^2=CH_3$; $R^3=C_2H_5$; $R^4=H$
i. $R^1=H$; $n=m=1$; $R^2=R^3=CH_3$; $R^4=H$
and wherein one of the dotted lines stands for a single carbon-carbon bond and the other one for a double bond, or each of them designates a single bond.

2. (−)-(E)-3,3-dimethyl-5-(2',2',3'-trimethyl-3'-cyclopenten-1'-yl)-4-penten-2-ol.

3. (−)-(1'S,E)-3-ethyl-3-methyl-5-(2',2',3'-trimethyl-3'-cyclopenten-1'-yl)-4-penten-2-ol.

4. (+)-(1'S)-2-methyl-4-(2',2',3'-trimethyl-3'-trimethyl-3'-cyclopenten-1'-yl)-1-pentanol.

5. (−)-(1'R)-2-methyl-4-(2',2',3'-trimethyl-3'-cyclopenten-1'-yl)-4-hexen-1-ol.

6. (−)-(1'S)-2-methyl-4-(2',2',3'-trimethyl-3'-cyclopenten-1'-yl)-4-penten-1-ol.

7. (−)-(1'S,E)-2-ethyl-2-methyl-4-(2',2',3'-trimethyl-3'-cyclopenten-1'-yl)-3-buten-1-ol.

8. (−)-(1'S,E)-2,2-dimethyl-4-(2',2',3'-trimethyl-3'-cyclopenten-1'-yl)-3-buten-1-ol.

9. (−)-(1',S)-2-ethyl-2-methyl-4-(2',2',3'-trimethyl-3'-cyclopenten-1'-yl)-1-butanol.

10. (+)-2,2-dimethyl-4-(2',2',3'-trimethyl-3'-cyclopenten-1'-yl)-1-butanol.

11. A perfume composition, a perfume base and a perfumed product containing as odor imparting or modifying ingredient an odor effective amount of one of the compounds according to claim 1.

12. A perfumed product according to claim 11 selected from the group consisting of soap, liquid and solid powder detergent and fabric softener.

* * * * *